United States Patent [19]

Kubo et al.

[11] 4,262,675

[45] Apr. 21, 1981

[54] BLOOD PRESSURE MEASURING INSTRUMENT HAVING COMPENSATION CIRCUIT

[75] Inventors: Kimio Kubo, Nara; Ryuichi Miyamae, Yamatokoriyama, both of Japan

[73] Assignee: Sharp Kabushiki Kaisha, Osaka, Japan

[21] Appl. No.: 964,954

[22] Filed: Nov. 30, 1978

[30] Foreign Application Priority Data

Nov. 30, 1977 [JP] Japan .................. 52-145326

[51] Int. Cl.³ ........................................... A61B 5/02
[52] U.S. Cl. ................................................. 128/680
[58] Field of Search .................... 128/680–685; 73/708; 364/415–417, 558, 571, 573, 608, 718, 851–852, 860

[56] References Cited

U.S. PATENT DOCUMENTS

| | | | |
|---|---|---|---|
| 3,662,163 | 5/1972 | Miller et al. | 364/573 |
| 3,700,865 | 10/1972 | Ley | 364/573 |
| 3,790,910 | 2/1974 | McCormack | 364/558 |
| 3,860,168 | 1/1975 | Byrd et al. | 364/571 |
| 3,920,004 | 11/1975 | Nakoyama et al. | 128/680 |
| 3,958,108 | 5/1976 | Shimomura | 364/558 |
| 4,078,551 | 3/1978 | Wohltjen et al. | 128/681 |
| 4,089,058 | 5/1978 | Murdock | 364/571 |
| 4,105,021 | 8/1978 | Williams et al. | 128/683 |
| 4,116,230 | 9/1978 | Gorelick | 128/682 |
| 4,137,907 | 2/1979 | Jansen et al. | 128/681 |

OTHER PUBLICATIONS

Fiegel, L. J., "Portable Blood Pressure Monitor", IBM Tech. Discl. Bulletin, vol. 9, No. 6, Nov. 1966, pp. 558–559.

Primary Examiner—Robert W. Michell
Assistant Examiner—Francis J. Jaworski
Attorney, Agent, or Firm—Birch, Stewart, Kolasch & Birch

[57] ABSTRACT

A sphygmomanometer includes a blood pressure detector, a compensation circuit for providing polygonal line approximation functions suitable for piezo-electric characteristics of the blood pressure detector according to compensation data externally applied thereto, and a pressure determination circuit for determining pressure values using the polygonal line approximation functions from the values measured by the blood pressure detector for a predetermined time period.

8 Claims, 16 Drawing Figures

BLOOD PRESSURE MEASURING INSTRUMENT HAVING COMPENSATION CIRCUIT

BACKGROUND OF THE INVENTION

The present invention relates to a blood pressure measuring instrument, e.g. a sphygmomanometer and, more particularly, to a compensation circuit for such a blood pressure measuring instrument for detecting the Korotkoff sound without suffering variations in the piezo-electric properties.

In a conventional sphygmomanometer, there was provided a pressure sensor for determining the blood pressure and developing an oscillation frequency corresponding to the same. Piezo-electric elements of the pressure sensor was utilized for converting an amount of the blood pressure into the oscillation frequency. However, the piezo-electric elements inevitably suffer variations and nonlinear properties. This necessarily requires accurate examination and modifications in the pressure sensor.

OBJECTS AND SUMMARY OF THE INVENTION

Accordingly, it is the primary object of the present invention to provide a highly reliable sphygmomanometer.

It is another object of the present invention to provide an improved sphygmomanometer where the necessity of examination and modification procedures are completely eliminated.

It is still another object of the present invention to provide an improved sphygmomanometer whose piezo-electric properties are controlled to compensate for variations and nonlinear properties by electronic techniques.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a sphygmomanometer comprises a variation compensation and a lineality compensation circuit. The variation compensation circuit is provided for cancelling variations in piezo-electric properties of a pressure sensor equipped with a sphygmomanometer. The lineality compensation circuit is utilized for compensating for nonlinear properties in the piezo-electric properties of the same.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DESCRIPTION OF THE PREFERRED EMBODIMENTS

Figure 1:
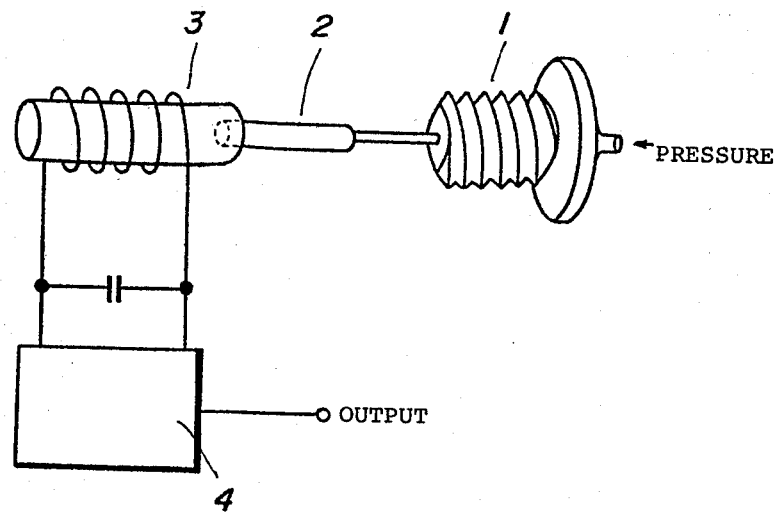
FIG. 1 is a perspective view of a pressure sensor showing a principle of the same.
Figure 2:
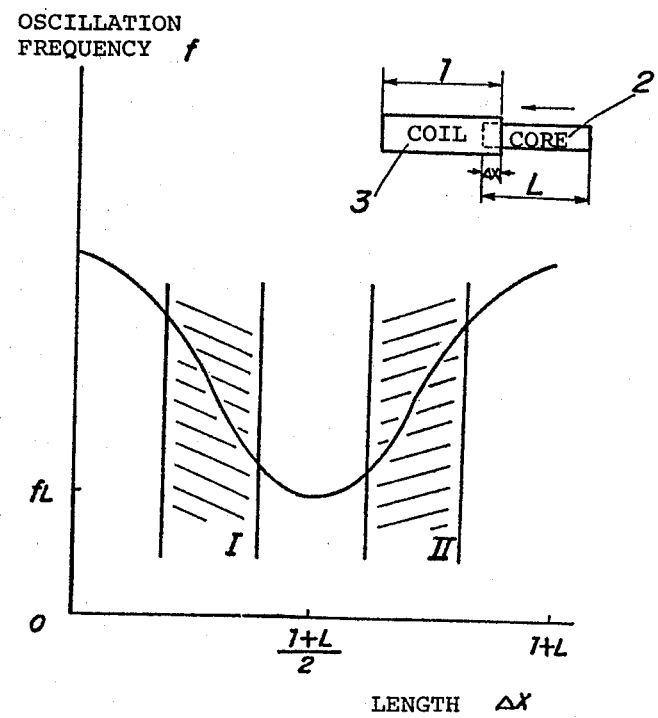
FIG. 2 is a diagram of output properties of the pressure sensor illustrated in FIG. 1.
Figure 3:
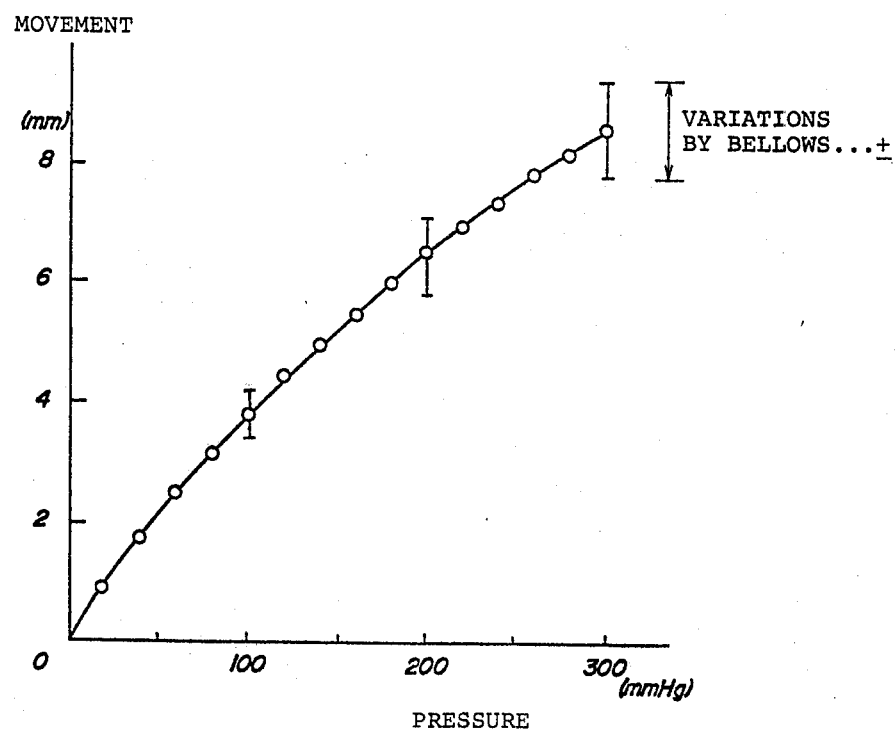
FIG. 3 is a diagram of movement properties of a bellows included within the pressure sensor.
Figure 4:
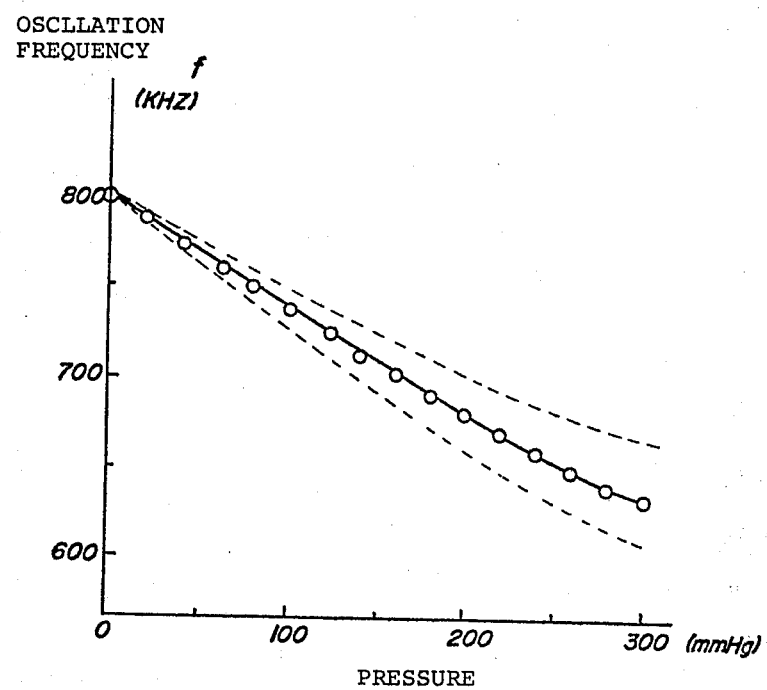
FIG. 4 is a diagram of oscillation properties of the pressure sensor.

FIG. 1 shows a pressure sensor adapted to the present invention, FIG. 2 is a graph of output characteristics of the pressure sensor shown in FIG. 1, FIG. 3 is a graph of movement characteristics of a bellows employed within the pressure sensor, and FIG. 4 is a diagram of frequency properties of the pressure sensor.

With reference to FIG. 1, the pressure sensor comprises a bellows 1, a core 2, a coil 3, and an oscillation circuit 4. The bellows 1 lengthens and shrinks responsive to applied pressure. The core 2 is disposed at the tip of the bellows 1. The core 2 is removed within a cavity portion of the coil 3. The inductance of the coil 3 is varied in accordance with the displacement of the core 2 to change oscillation frequency developed from the oscillation circuit 4, according to movement of the bellows 1.

The data in FIG. 2 are plotted with oscillation frequency on ordinate and the length $\Delta \chi$ of a portion of the core 2 inserted into the coil 3 on abscissa. L is the length of the core 2 and l is the total length of the coil 3.

The value of the oscillation frequency f is a minimum as represented by $f_L$ when $\Delta \chi = (L+l)/2$ because the inductance of the coil 3 is a maximum.

The data in FIG. 2, in general, has a parabolic curvature with an axis of $\Delta \chi = (L+l)/2$ and slightly linear characteristics in two portions depicted in the regions I and II.

FIG. 3 shows a graph showing typical found values in the movement of the bellows 1 according to the applied pressure between zero and 300 mm Hg. As is viewed in FIG. 3 there are variations of the found values in the bellows 1 between ±10% by manufacturing conditions for the bellows 1. However, these variations allow the slope of the characteristic graph to only change. In other words, no two characteristics lines cross each other.

It will be apparent from FIGS. 2 and 3 that the movement of the bellows 1 is saturated according to the increase in the applied pressure and the change in the oscillation frequency should be referred to in the section of FIG. 2 where the change in the oscillation frequency of the bellows changes according to the variation in the length of the overlap $\Delta\chi$.

FIG. 4 represents by solid line oscillation properties of the pressure sensor which is manufactured for the test under the above-mentioned condition. As is apparent from FIG. 4, the error is estimated to be the worst within ±1 mmHg even if a line is utilized for making an approximation at the section defined by the pressure between zero to 100 mmHg. In connection with the pressure above 100 mmHg, the oscillation properties show slightly saturated conditions which cause the bellows to fail to hold completely its lineality properties. The dotted lines of FIG. 4 show other undesirable characteristic properties with different slopes due to the variations in the manufacturing conditions and/or the variations in the location of the coil 3 and the core 2.

Figure 5:
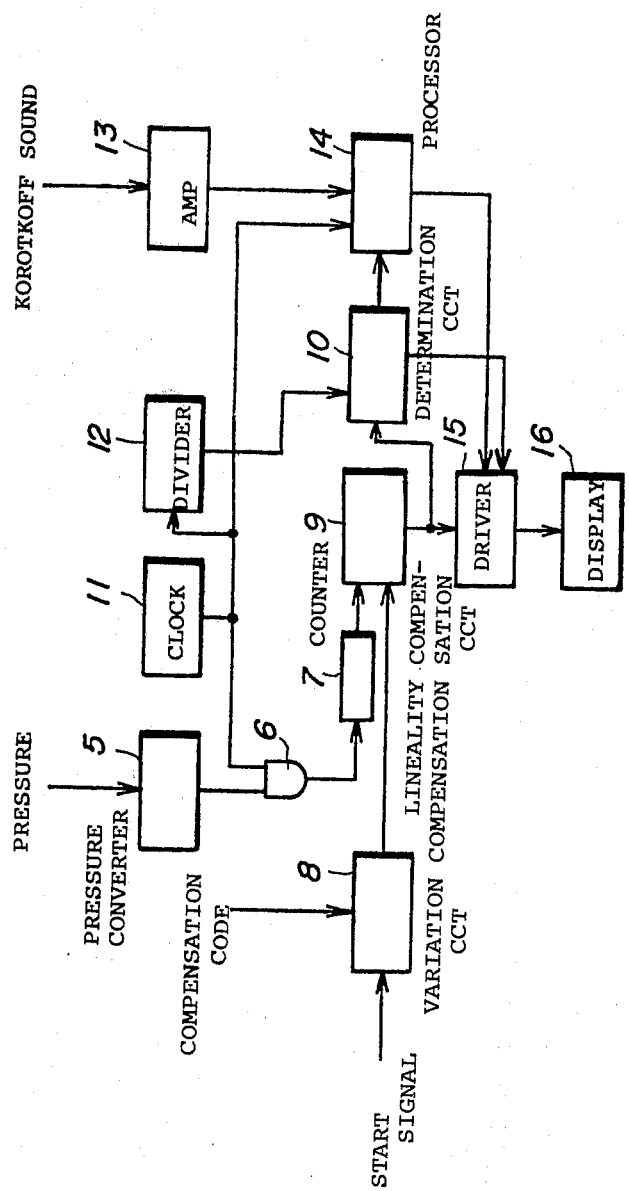
FIG. 5 is a block diagram of a control circuit of a sphygmomanometer according to the present invention.

Now with reference to FIG. 5, there is shown a block diagram of a control circuit of a digital sphygmomanometer according to the present invention. The control circuit comprises a pressure converter 5 referred to the pressure sensor, a counter 7, a variation compensation circuit 8, a lineality compensation circuit 9, a determination circuit 10, a clock circuit 11, a divider 12, an amplifier 13, a processor 14, a driver 15, and a display 16. The output of the pressure converter 5 is applied to the counter 7 through a gate 6. The variation compensation circuit 8 functions to generate polygonal line approximation functions corresponding to the pressures detected by the pressure sensor by modifying a reference polygonal line approximation function according to modification codes applied thereto.

The lineality compensation circuit 9 serves to calculate pressure values corresponding to the modified polygonal line approximation functions by information detected by the pressure sensor for a predetermined time period. The determination circuit 10 is operated to determine both the increase and the decrease of the pressure and whether or not the present pressure is 20 mmHg or more, thereby providing respective control signals. The amplifier 13 operates to amplify and normalize the Korotkoff sounds sensed by a microphone (not shown) to thereby provide the output impressed onto the processor 14. The processor 14 is provided for picking up the true Korotkoff sounds and applying them to the driver 15. The display 16 indicates systolic and diastolic pressures responsive to the output of the driver 15.

The operation of the control circuit is described with reference to a time chart shown in FIG. 6. Assumed that the modification codes are preset to be suitable for the pressure sensor equipped within the system, a start signal is applied to the variation correction circuit 8 in response to the energization of the power supply. The variation compensation circuit 8 sets a polygonal line approximation function according to the modification codes. The pressure converter 5 provides different oscillation frequencies depending on the relative pressure.

The clock circuit 11 develops clock signals 17 having a small duty factor which functions to make the gate 6 conductive. The counter 7 counts the oscillation frequency. The lineality compensation circuit 9 makes lineality compensation according to a timing signal 22 after the counting is completed. The data is transferred into the determination circuit 10 and the driver 15. The determination circuit 10 determines whether the relative pressure is 20 mmHg or more. The determination circuit 10 further compares the now received data to the previously present data which is sensed in the previous timing, using the comparison timing developed by the divider 12. The system thereby senses an increase or decrease in the pressure. When the pressure data is below 20 mmHg, the determination circuit 10 develops reset signals for the driver 15. If the pressure data is determined to be decreasing as compared to the same in the preceding time period, pressure decrease recognition signals generated from the determination circuit 10 are impressed into the processor 14. The processor 14 recognizes the signals developed from the amplifier 13 to determine if they are true Korotkoff sounds using the timer means contained therein and the signals derived from the determination circuit 10. The results by the processor 14 are transferred into the driver 15. The driver 15 controls the timing where the data derived from the lineality compensation circuit 9 is indicated in the display 16, depending on the data developed from the determination circuit 10 and the processor 14.

Blood pressure measuring procedures are traced according to pressure change 10 of FIG. 6 as follows. While there is no pressure, a first indicator I referred to an indicator for showing systolic pressure is blank condition 20. A second indicator II normally displays the pressure data which is now measured and it indicates diastolic pressure when the diastolic pressure is detected. The second indicator II displays zero pressure or the diastolic pressure in the preceding measuring procedure in the timing 21 while the measured pressure is less than 20 mmHg.

While the measured pressure is 20 mmHg or more, the pressure data determined by the pressure sensor is lineality compensated using lineality compensation timing signals 22 and the results are transferred, for displaying purposes, into the second indicator II each time the calculation is completed. The decrease of the pressure data is recognized by comparing the pressure data introduced into the determination circuit 10 at a timing 24 with the same at the preceding timing 25. Upon the detection of the decrease of the pressure data, the pressure decrease recognition signals are introduced from the determination circuit to the processor 14.

Figure 6:
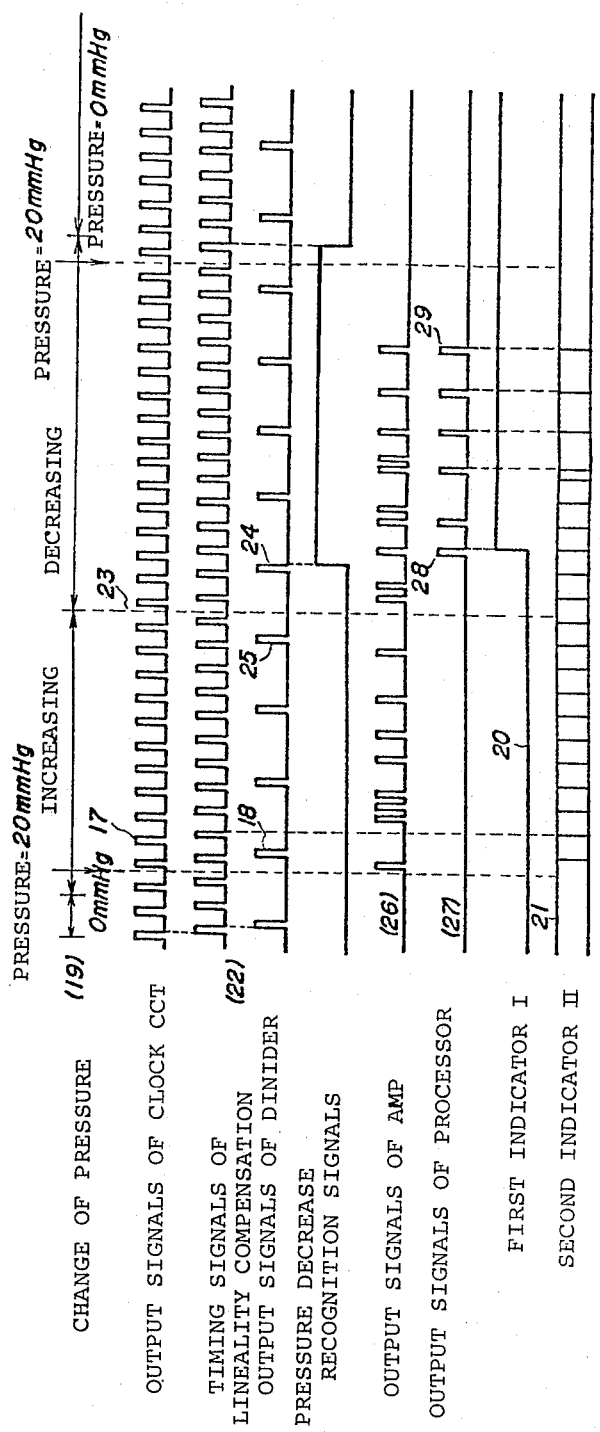
FIG. 6 is a time chart of various signals occurring in the control circuit shown in FIG. 5.

Since the microphone for collecting the Korotkoff sound inevitably detects various noise, the output of the amplifier 13 necessarily contains noise signals except for signals in synchronization with pulsation as viewed in amplifier output signals 26 of FIG. 6. Therefore, the true Korotkoff sound is obtained by executing the AND logic operation on the pressure decrease recognition signals and the amplifier output signals 26 and further eliminating, using the timer means, noise signals contained in pressure decreasing time periods. Processor output signals 27 are true Korotkoff sound.

The driver 15 allows the first indicator I to indicate and retain the present pressure data as the systolic pressure, assuming that the first signal 28 of the processor output signals 27 is the first Korotkoff sound. The second indicator II, on the other hand, goes on refreshing the display data in synchronization with the output signals of the processor 14. The second indicator II displays the relevant pressure data as the diastolic pressure only when the last signal 27 of the processor output signals 27 is regarded as the last Korotkoff sound. The determination whether a further Korotkoff sound is present or absent is affirmed by not receiving the output signals from the processor 14 with the elapse of a predetermined time period of the generation of the last signal 29.

The variation compensation circuit 8 and the lineality compensation circuit 9 are now described in detail hereinbelow. First of all, the principle of compensation utilized therein is explained. The principle is described using methods of least squares with reference to a model of conversion characteristics in the present sensor shown in FIG. 7. In these statistical researches, the evaluation of errors in found values is conducted after compensation functions are defined according to the given data. However, the evaluation of the errors is not necessarily required and, instead, the most suitable correlation functions are available within a given range of errors and regions of two kinds of transformation are determined which are available for the correlation functions.

Trial and error procedures by a computer are suitable for obtaining the relevant correlation functions relied upon the given errors and, simultaneously, defining the regions where thus obtained correlation functions are available. At first, values of allowed errors are assumed in accordance with the accuracy of the instruments. Thereafter, the regions are desirably selected where the correlation functions are defined.

Figure 7:
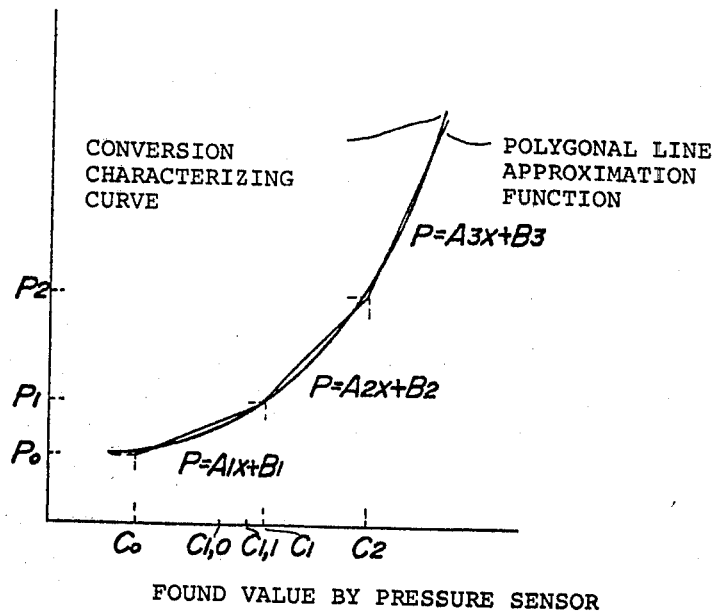
FIG. 7 is a diagram of conversion properties of the pressure sensor showing a model of the conversion properties.

With reference to FIG. 7, values C1, 0 and C1, 1 of the found value X of the pressure sensor are desirably selected and the found value X defined by the region $C0 \leq X \leq C1, 0$ is considered as below. A correlation function (a linear function $y = m x + b$) is utilized for assuming the data measured by the pressure sensor. Another correlation function is defined by making difference values between the found values and the linear function and adding least squaring of the respective difference values each other and, at last, being selected to minimize the added results. The evaluation of the error in the found values by the pressure sensor is effected according to the obtained correlation function over the region $C0 \leq X \leq C1, 0$ to compare the measured error with the allowed error.

Another value C1, 1 smaller than the value C1, 0 is selected when the values of the measured error are more than the allowed error and vice versa. The above-mentioned mathematical procedures are repeated until the values of the measured error is equal to that of the allowed error. This repetition is provided within the given allowed error both the correlation functions having the widest variation region and the measuring region available by the pressure sensor.

Referring now to FIG. 7, this means that a plurality of coefficients C1, A1, and B1 are defined in $C0 \leq X \leq C1$ and $P = A1X + B1$. A plurality of equations $P = A2X + B2 \ldots P = ANX + BN$ are determined in the respective sections by repeating the preceding procedures in the sections $C1 \leq X \leq C2$, $C2 \leq X \leq C3 \ldots$, $CN - 1 \leq X \leq CN$. It is preferable in obtaining the correlation function $P = A2X + B2$ in the section $C1 \leq X \leq C2$ that the correlation function $P = A2X + B2$ be continuous at $X = C1$ with the correlation function $P = A1X + B1$. The condition of accomplishing the continuous connection at $X = C1$ is $B2 = (A1 - A2)C1 + B1$, e.g. to require defining the values A2 and C2.

The repetition of the above-mentioned procedures over the total sections of measuring procedures by the pressure sensor provides a series of polygonal line correlation functions which are referred to conversion characterizing curves within the allowed error for converting from the pressure by the pressure sensor to electrical signals. The polygonal line correlation functions are linear functions and continuous with each other. These are referred to polygonal line approximation functions. At a plurality of sectional points DK ($K = 0, 1, 2, \ldots N$), the polygonal line correlation functions show different slopes. The values of the pressure at the respective sectional points are derived from the equations $P_0 = A1C_0 + B1$, $PK = AK \cdot CK + BK$ ($K = 1, 2, \ldots, N$). The respective polygonal line correlation functions are featured by the pressure values PK at the respective sectional points and the found values CK (converted value) by the pressure sensor corresponding to the pressure value PK.

Figure 8:
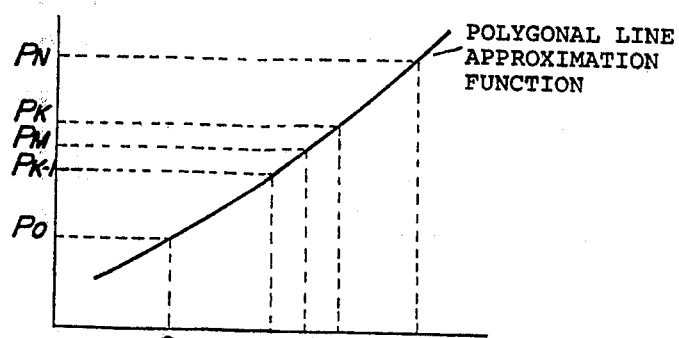
FIG. 8 is a diagram of a polygonal line approximation function for the pressure sensor.

Using the thus derived polygonal line approximation functions, the pressure values are determined by the found values measured by the pressure sensor as described below. It is assumed that the polygonal line approximation functions as illustrated in FIG. 8 are obtained under the data PK and CK at the respective sectional points ($K = 0, 1, 2, \ldots, N$). A found value CM is measured by the pressure sensor in assumptions. The logical principle for changing from the found value CM to the pressure value is assumed as follows.

The data CK and PK at the respective sectional points are subsequently stored in a memory circuit. The comparison between the found value CM and the data CK ($K = 0, 1, \ldots, N$) at the respective sectional points is conducted within a comparator to determine which sectional regions contain the found value CM. The following calculation is carried out at the detected sectional region for the found value CM.

$$PM = P_{K-1} + \frac{Pk - Pk - 1}{Ck - Ck - 1} (CM - Ck - 1) \quad (1)$$

$$= P_k - \frac{Pk - Pk - 1}{Ck - Ck - 1} (Ck - CM) \quad (2)$$

The above two equations are mathematically equivalent to each other. However, this contains subtill differences in the manner of calculating PM. These differences can be eliminated by changing detection methods for determining which sectional regions include the found value CM.

Figure 9:
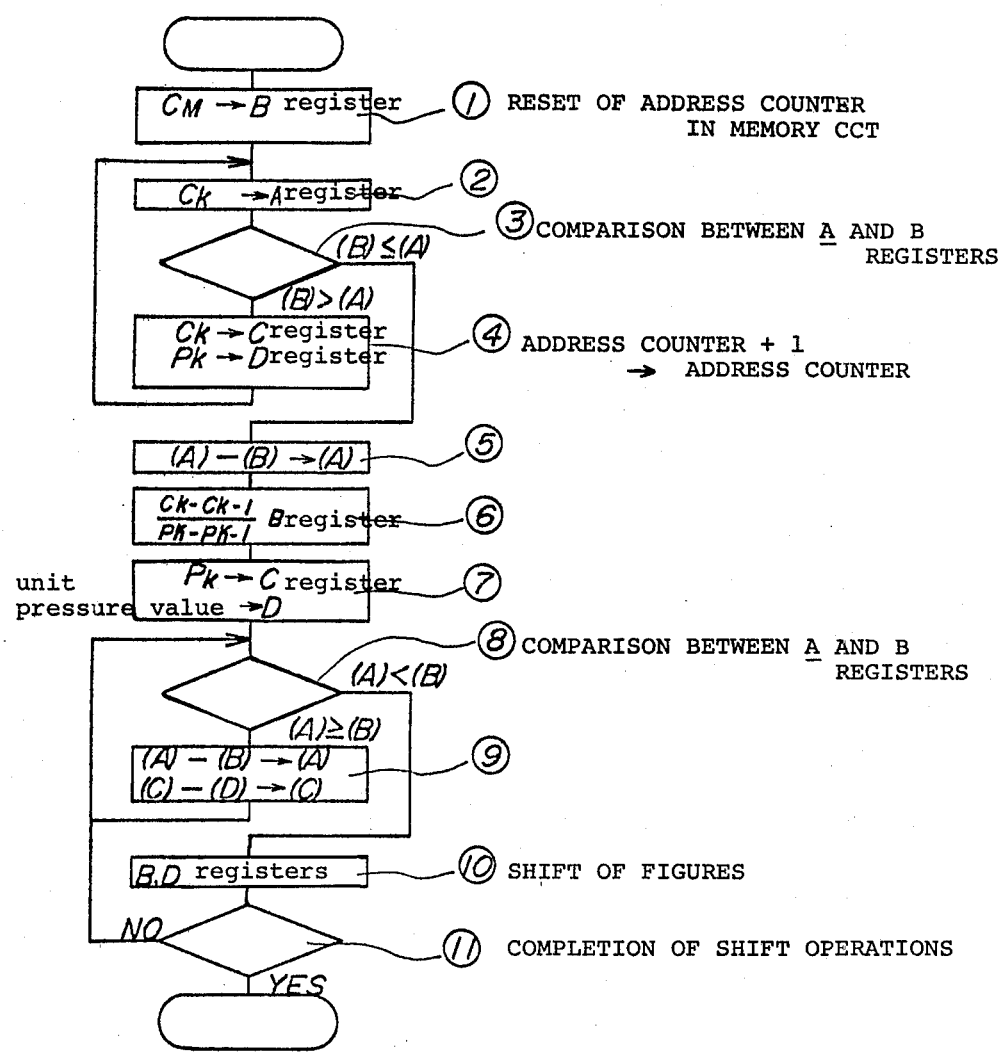
FIG. 9 is a flow chart showing calculation operations.

A flow chart of operating the calculation according to the equation (2) is depicted in FIG. 9. Four registers A, B, C, and D are utilized for conducting the calculation in the following order.

① The found value CM by the pressure sensor is transferred into the B register so that address counters of the memory circuit are allowed to be reset which store the data at the sectional points in the conversion characterizing curve of the pressure sensor.

② One of the measured values Ck is transferred into the A register, the measured value Ck being selected by the address counter. The measured values Ck is included within the conversion characterizing curve of the pressure sensor in the respective sectional points.

③ The comparison between the data contained in the A register and the same of the B register is carried out.

④ The data Ck and Pk selected by the address counter of the memory circuit are transferred respectively to the C and D registers, when the contents of the B register are more than that of the A register. The address counter of the memory circuit is advanced by one. Therefore, the procedure for transferring the data Ck into the A register is reproduced. This repetition is carried out until the contents of the A register are equivalent to or more than that of the B register.

⑤ When the contents of the A register are equivalent to or more than that of B register, the contents of the B register are subtracted from that of the A register and the results are retained in the A register.

⑥ The following calculation is carried out and the results are kept in the B register.

$$\frac{Ck - Ck - 1}{Pk - Pk - 1}$$

where the data $Ck-1$ and $Pk-1$ are stored respectively in the C and D registers, and the data Ck and Pk are selected at present by the address counter of the memory circuit.

⑦ The data Pk are introduced into the C register. The B register contains values of the variation of the measured values by the pressure sensor corresponding to an unit variation of the pressure. The unit of the data Pk and $Pk-1$ is, for example, mmHg, the B register includes the amount of the variation in the measured data by the pressure sensor corresponding to the change in pressure of 1 mmHg. This means that the data ten times the data contained in the B register are the amount of the variation in the measured values relied upon the change of the pressure of 10 mmHg. For the purposes of shortening calculation time periods, one unit reference pressure is defined as follows while the calculation of $$\frac{Ck - Ck - 1}{Pk - Pk - 1}$$

is carried out. The one unit of the reference pressure is approximately equivalent to the amount of the change in the pressure at the respective sections when the available regions selected from the conversion characterizing curve of the pressure sensor are divided into the number N. The D register is allowed to store the reference pressure (one unit of the pressure).

⑧ The above-mentioned data is completed and the comparison between the contents of the A register and that of the B register takes place.

⑨ When the contents of the A register are equivalent to or more than that of the B register, the contents of the B register are subtracted from that of the A register and the results are kept in the A register. The contents of the D register are subtracted from that of the C register and the results are stored in the C register. Therefore, the comparison between the contents of the A and B registers is reproduced. This cycles are repeated before the contents of the B register become more than equal to that of the A register.

⑩ When the above conditions are completed, shift operations are carried out in the B and D registers to reduce the order of the contents therein.

⑪ The completion of the calculation procedures is determined by either making completely setting of zero conditions in the D register or reducing the contents of the D register by one at each shifting procedure with a predetermined number of occurrence of the shifting procedures. If the completion does not reach, the comparison between the contents of the A and B registers are still carried out before the shifting procedures are terminated. The results of the above-mentioned calculation procedures are stored in the C register.

The following is an example for setting an unit of the pressure. It is rare that the divided sections of the convention characterizing curve of the pressure sensor have equivalent intervals each other. However, it is assumed for convenience that the variation in the pressure at one of the sections is about 80 mmHg. The unit of the pressure is set to be several tens mmHg as described previously. The unit of the pressure is available in 10, 20, 30 mmHg or the like. The amounts of the variation in the data measured by the pressure sensor per the variation of an unit of the pressure (1 mmHg) are calculated by the following equation.

$$\frac{Ck - Ck - 1}{Pk - Pk - 1} = \frac{Ck - Ck - 1}{80}$$

The B register receives the amounts ten or twenty times the above-determined values. 10 mmHg or 20 mmHg are set for the D register.

Figure 10:
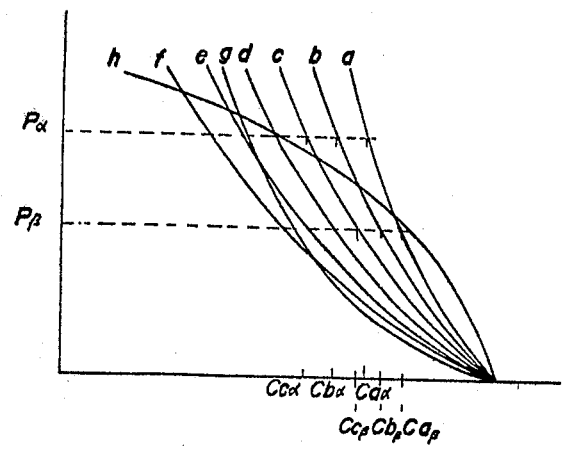
FIG. 10 is a graph of a model of experimental measurements by the pressure sensor.

The principle for compensating for the variation in the pressure sensor is described hereinbelow. FIG. 10 shows in model manners tendency of the variations in the found values of the pressure sensor where a plurality of characterizing curves a to f exist in general and a characterizing curve g is rare and another characterizing curve h is not in practice measured. Logical correction is, therefore, applied to the characterizing curves a to f not to g and h.

In FIG. 10, it is assumed that when the different pressure Pα and Pβ are measured by three kinds of pressure sensors a, b, and c, the found values Caα, Caβ, Cbα, Cbβ, Ccα and Ccβ are obtained. The following correlation is experimentally confirmed between these found values.

$$\frac{Cc\alpha - Ca\alpha}{Cc\alpha - Cb\alpha} = \frac{Cc\beta - Ca\beta}{Cc\beta - Cb\beta} = \text{constant} \qquad (3)$$

The correction principle is relied upon the equation (3). The following equation (4) is obtained from the equation (3).

$$\left. \begin{array}{l} Cc\alpha - Ca\alpha = \text{constant} \times (Cc\alpha - Cb\alpha) \\ Cc\beta - Ca\beta = \text{constant} \times (Cc\beta - Ca\beta) \end{array} \right\} \qquad (4)$$

Considering that the lineality compensation is carried out with reliance upon the polygonal line approximation functions, it is preferable that the values α and β correspond to desired sectional points because the values α and β are arbitrary values. Using the equation (4), the data Caα and Caβ at the sectional points can be calculated for identifying the polygonal line approximation function if a reference polygonal line approximation function C, a polygonal line approximation function b on a desired characterizing curve and the constant are determined. Therefore, a polygonal line approximation function a is defined to determine an amount of (Ccα−Cbα) in the equation (4). Now the amount of (Ccα−Cbα) is referred to a reference correction value for determining purposes. The constant in the equation (4) is selected to be effective only in its integral number in a relationship with the allowed error. Code performance used herein means that compensation amounts are converted into a constant using the reference correction value and thus converted constant is termed codes. Therefore, the compensation amounts can be represented using less kinds of amounts to make broad compensation applications to be available. This can be referred to a kind of the compression for the data.

Figure 11:
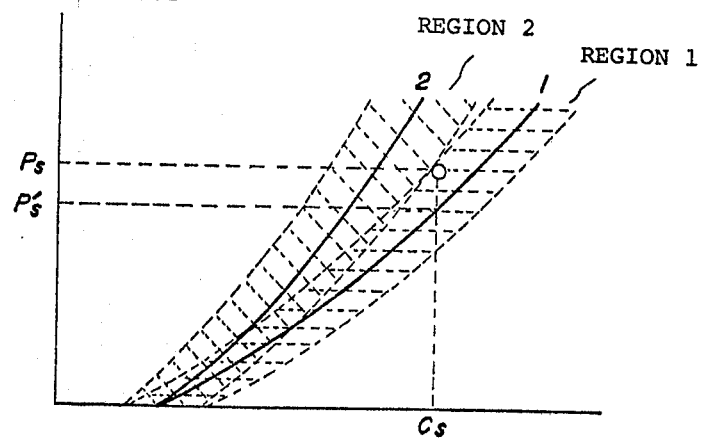
FIG. 11 is a graph showing compensation principles for the variations of the pressure sensor.

FIG. 11 is utilized for explaining the reasonableness of the compensation principle for the variation, where a polygonal line approximation function 1 is selected on the base of characteristics of a pressure sensor. A measured value Cs is obtained by measuring a pressure Ps using another pressure sensor. The measured value Cs is linearly approximated by the polygonal line approximation function 1 to obtain the results P's calculated by the lineality compensation circuit. However, the pressure Ps can be assumed to be equivalent to the pressure P's if the following inequality (5) is set up.

$$|Ps - P's| < \text{allowed error} \quad (5)$$

The linearlity compensation on the base of the polygonal approximation function 1 is finally available in the region 1 which is depicted by dotted lines in FIG. 11. This means that the error of the lineality compensation is within the allowed error regarding the various characteristics included within the region 1 of FIG. 11 if the polygonal line approximation function 1 is utilized for approximating purposes. If the region 1 is not available, another region 2 is considered to define another suitable polygonal line approximation function 2. It will be apparent that the region 2 is preferably selected to be contact with the region 1. The extent of the region 2 is, of course, determined according to the inequality (5). The compensation of the variation in the characteristics of the pressure sensor is widely possible by repeating the above-mentioned procedures. To determine the regions, it is necessary to define the respective polygonal line approximation functions characterizing the regions.

As described previously concerning the definition of the code performance and the reference compensation amounts, the polygonal line approximation functions are determined with reliance upon the spaces of the reference compensation amounts. Therefore, the respective polygonal line approximation functions are defined according to the reference compensation amounts so that the regions are fixed where the respective polygonal approximation functions are effective.

There is a restriction regarding the determination of the reference compensation amounts. The following is the fluctuation in the found values by the pressure sensor in measuring the same pressure on the base of the allowed error in the same polygonal line approximation function.

$$\pm(\text{the allowed error} \times \text{the slope of the polygonal line approximation function}) \quad (6)$$

On the other hand, the following relationship is valid.

The reference correction amounts > (the allowed error × the slope of the polygonal line approximation function K) + (the allowed error × the slope of the polygonal line approximation function K + 1) (7)

The latter ≃ 2 × (the allowed error × the slope of the polygonal line approximation function K) (8)

The approximation of the equation (8) is applied when the slope of the polygonal line approximation function does not change. When the reference compensation amounts are fixed under the conditions of the inequality (7), there is unfortunately at least one region which is not corrected (has an error more than the allowed error) to provide dissatisfactory results. The reference compensation values should be selected to be valid in the following inequality (9).

The reference correction values < (the allowed error × the slope of the polygonal line approximation function K) + (the allowed error × the slope of the polygonal line approximation function K + 1) (9)

Two pressure sensor a and b which have different characteristics each other measure the pressure to determine the polygonal line approximation functions. The value $\alpha$ is defined according to the found values Ca and Cb by the pressure sensor at the sectional points at which the maximum of the compensation values is needed as follows.

$(Ca - Cb)/\alpha < 2 \times (\text{the allowed error} \times \text{the slope of the polygonal line approximation functions a or b})$ (10)

The reference correction value Mk [k=0, 1, 2, ..., N (k is the number of the sectional points)] is determined by the following equation (11).

$$Mk = 2 \frac{Cak - Cak}{\alpha} \quad (k = 0, 1, 2, \ldots, N) \quad (11)$$

The standard for the compensation is required to introduce the principle. The determination of the reference polygonal line approximation functions, which are polygonal line approximation function as the standard for the compensation, has a relationship with the effective utilization of the compensation codes. It will be apparent that the selection of the reference polygonal ling approximation function is effectively fixed by either the characterizing curves of the pressure sensor emerged at the ends of the region where the pressure sensor reveals its characteristics or ordinary characterizing curve. With reference to FIG. 10, the utilized characterizing curves are referred to a or f, otherwise, c or d.

Figure 12:
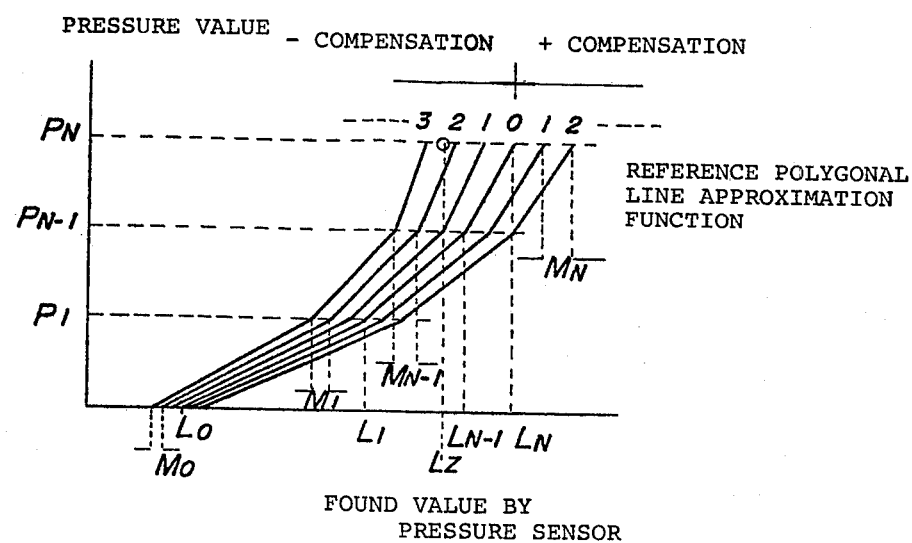
FIG. 12 is a graph showing reference polygonal line approximation functions and correction amounts.

FIG. 12 depicts in a mode manner one reference polygonal line approximation function 0 and the reference compensation value Mk (k=0, 1, ..., N) in the respective sectional points assuming the found values of several tens. The data of the reference polygonal line approximation function in the respective sectional points is the found values Lk (k=0, 1, ..., N) of the pressure sensor concerning the pressure value Pk. To determine the codes for one pressure sensor, the pressure is increased to suitable sectional points. The value $\alpha$ is calculated by the following equation.

$$\alpha = 2 \frac{Lz - Ln}{Mn} \quad (12)$$

where Lz is the found value of the pressure sensor when the pressure is increased to PN in FIG. 10.

The codes are selected in accordance with the value $\alpha$ as follows.

| code 0  | in $|\alpha| \leq 1$       | (13) |
|---------|----------------------------|------|
| code 1  | in $1 < \alpha \leq 3$     |      |
| code −1 | in $-3 \leq \alpha < -1$   |      |
| code 2  | in $3 < \alpha \leq 5$     |      |
| code −2 | in $-5 \leq \alpha < -3$   |      |

-continued and so on

The code of FIG. 12 is selected to be 2 since the value α is nearly 4 by eye-measurement. The selection of the extent of the value α is equivalent to the establishment that the region, where the respective polygonal line approximation functions are effective in FIG. 9, is determined to be of ±Mk/2 in the respective sectional points with having a center based on the polygonal line approximation functions corrected by the reference polygonal line approximation function in the respective sectional points.

Figure 13:
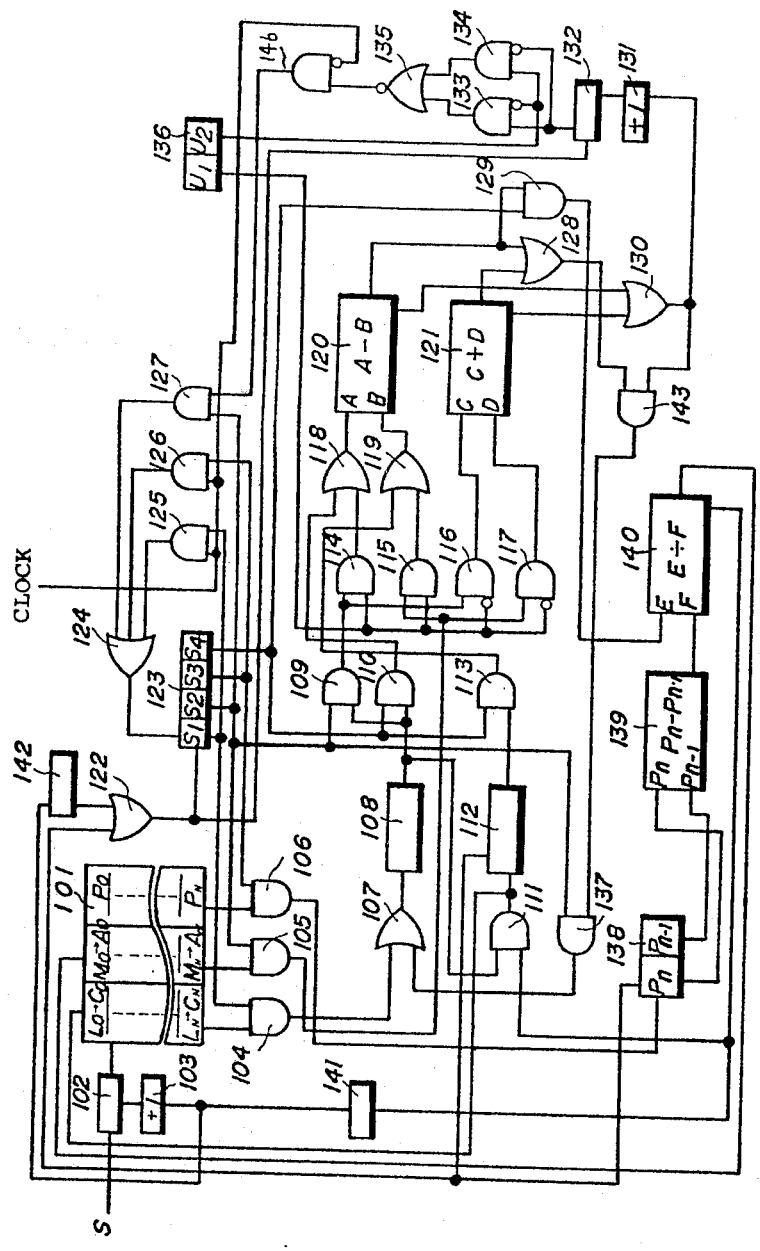
FIG. 13 is a circuit configuration of a variation compensation circuit according to the present invention.
Figure 14:
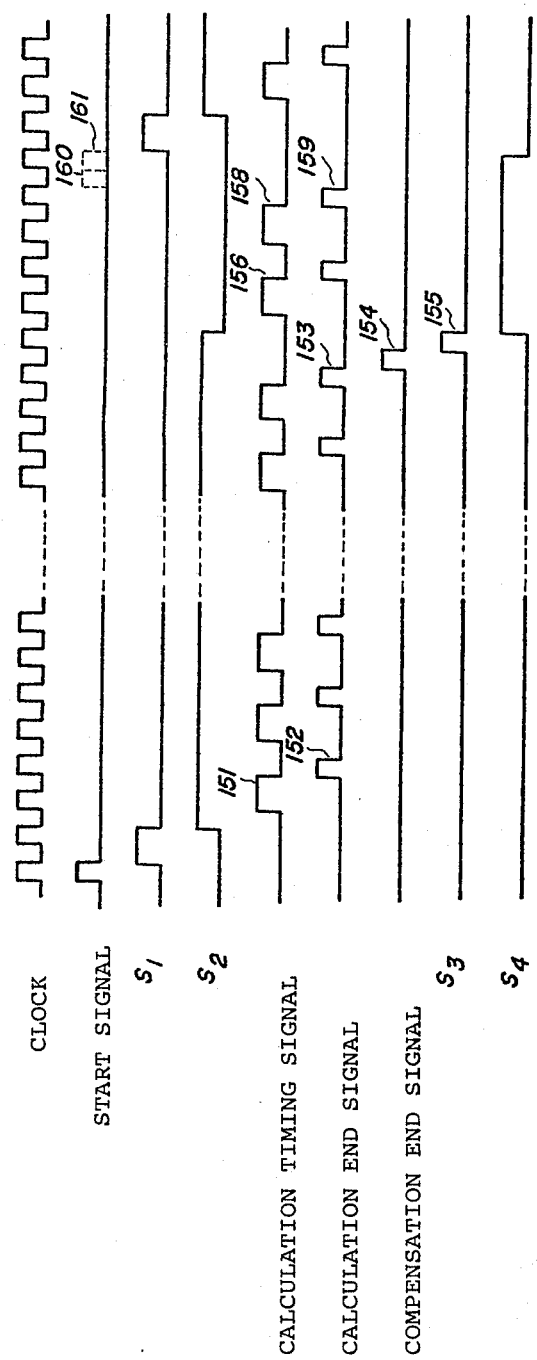
FIG. 14 is a time chart of various signals occurring in the variation compensation circuit shown in FIG. 13.

Specific circuits and operations of the variation compensation circuit and the lineality compensation circuit for the characteristics of the pressure sensor are described in detail hereinbelow. FIG. 13 shows a circuit configuration of the variation compensation circuit and FIG. 14 is a time chart of various signals occurring in the variation compensation circuit illustrated in FIG. 13. The operations of the variation compensation circuit shown in FIG. 13 are explained, for example, with reference to the model of the compensation depicted in FIG. 12. It is assumed that a memory circuit contains the data Lk and Pk of the reference polygonal line approximation function in the respective sectional points and the reference compensation value Mk in the respective sectional points in the order of from k=0 to k=N. A register 136 to store compensation codes is externally set up to comprise two kinds of registers U1 and U2. The register (1) is a code register of a bit to direct the direction for compensation. The register U2 is a register for the codes of four bits. It is possible to allow the reference polygonal line approximation function to be compensated over 30 steps by the register 136.

Upon the application of a start signal S into an address counter 102, all of the address counter 102, a counter 132, a register 112, and a shift register 138 are turned reset. A shift register 123 (S1, S2, S3, S4) is set to be (1000) at the trailing of the start signal S. The condition of S1=1 is retained for one clock time period after the trailing of the start signal S. Meanwhile, the data Lo are introduced into a register 108 through a gate 104. A gate 125 is operated to permit the shift register 123 to advance the contents to (0100) by making AND logic operation between the signal S1 of the shift register 123 and the clock. The condition of (0100) makes a gate 105 conductive. Gates 114 and 115 become conductive when the register U1 is "1" so that + compensation of FIG. 12 is carried out. Gates 116 and 117 become conductive when the register U1 is "0" to take place − compensation in FIG. 12.

A subtractor 120 and an adder 121 receive the data through these gates while a timing pulse 151 is generated to complete the calculation. One of the subtractor 120 and the adder 121 does not receive the data because of the nonconductiveness of the gate. Therefore, one of the following equations is completed but there is no problem because an AND gate 128 is provided for receiving these results from the subtractor 120 and the adder 121.

$\phi + \phi = \phi$ or $\phi - \phi = \phi$ where $\phi$ is representative of unstable conditions.

The calculation Lo±Mo (+ is referred to + compensation and − is − compensation) is carried out. The results are transferred from the operators 120 and 121 into a register 108 in synchronization with a calculation end signal 152 through gates 143 and 137. The calculation end signal 152 makes the counter 132 advance by one through a increment circuit 131. AND gates 133 and 134 and an OR gate 135 conduct exclusive OR between the counter 132 and lower digits U2 of the register 136. If the coincidence between the counter 132 and the degits U2 does not reach, the adder and subtractor of the compensation value Mo is repeated and, simultaneously, makes the counter 142 advance by one at each procedure of the calculation. This is repeated until the contents of the counter 132 are coincident with that of the register U2 of the register 136.

Upon the coincidence, a signal 154 is output on a line 146 at the trailing of the calculation and signal 153 in synchronization with the clock. The signal 154 makes it possible to transmit the shift register 125 into the condition of (0010). These processes provide the found values Co by the pressure sensor in the polygonal line approximation function to be seeked.

The condition of (0010) is kept for a half clock time period as indicated by another timing pulse 155. Meanwhile, the data Po are transferred into the shift register 138 through a gate 106. The data previously referred to Pn are shifted to that of Pn−1. When the shift register 123 is changed from (0010) to (0001), the contents of registers 108 and 112 are transmitted into the subtractor 120 through gates 110 and 113 at a timing pulse 156 to calculate "C0−0". The results are introduced into a divider 140 through a gate 129 at a timing pulse 158 and, simultaneously, the contents of a subtractor 139 are introduced into a divider 140. The calculation of $$A0 = \frac{C0 - 0}{P0 - 0}$$

is calculated.

The data A0 are transmitted into the memory circuit 101 instead of M0. The divider 140 generates the calculation end signal 159 at the trailing of a timing pulse 158 after the completion of the calculation.

A gate 111 becomes conductive and, meanwhile, the contents of the register 108 are transmitted into a register 112 to be utilized as the data Cn−1 for the following calculation. The calculation end signal 159 is delayed to a signal 160 through a delay circuit 141. The signal 160 permits the address counter 102 of the memory circuit 101 to advance by one. The signal 160 is further delayed into a signal 161 by a delay circuit 142. The signal 161 allows the shift register 123 to return back to the initial condition of (1000). The calculation for the data C1 and A1 follows the above-mentioned procedures.

The above is summarized as follows. The data Ln is transferred to the register 108 at S1=1 on the shift register 123. The calculation CN=LN−αMn (α is the compensation codes) is carried out at S2=1. The data Pn are transferred into the shift register 138 at S3=1. The calculation of (Cn−Cn−1)/(Pn−Pn−1) is taken place at S4=1 to be introduced into the memory circuit 101. The value of A0 is not always correct, since the data Cn−1 for calculating the value A0 becomes "0". The data including the data A0 should be erased when the data contained in the memory circuit 101 is utilized after the completion of the calculation. Thus the suitable polygonal line approximation functions are selected by performing the compensation directed by the compensation code.

Figure 15:
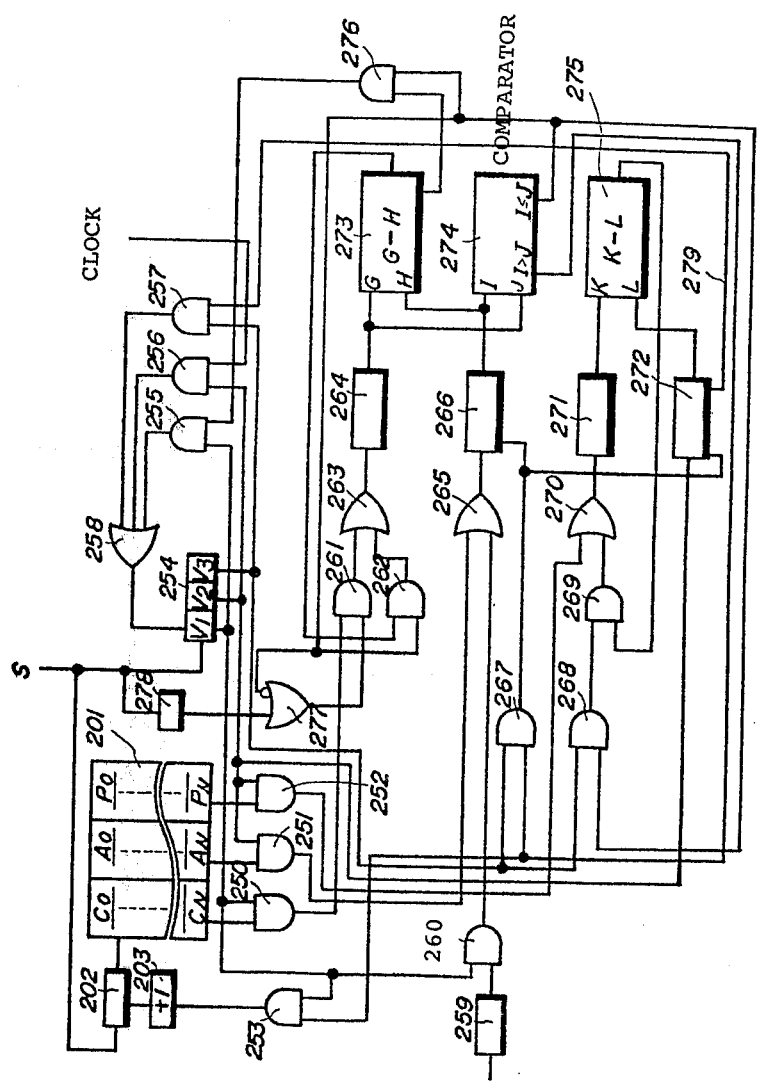
FIG. 15 is a circuit configuration of a lineality compensation circuit according to the present invention.
Figure 16:
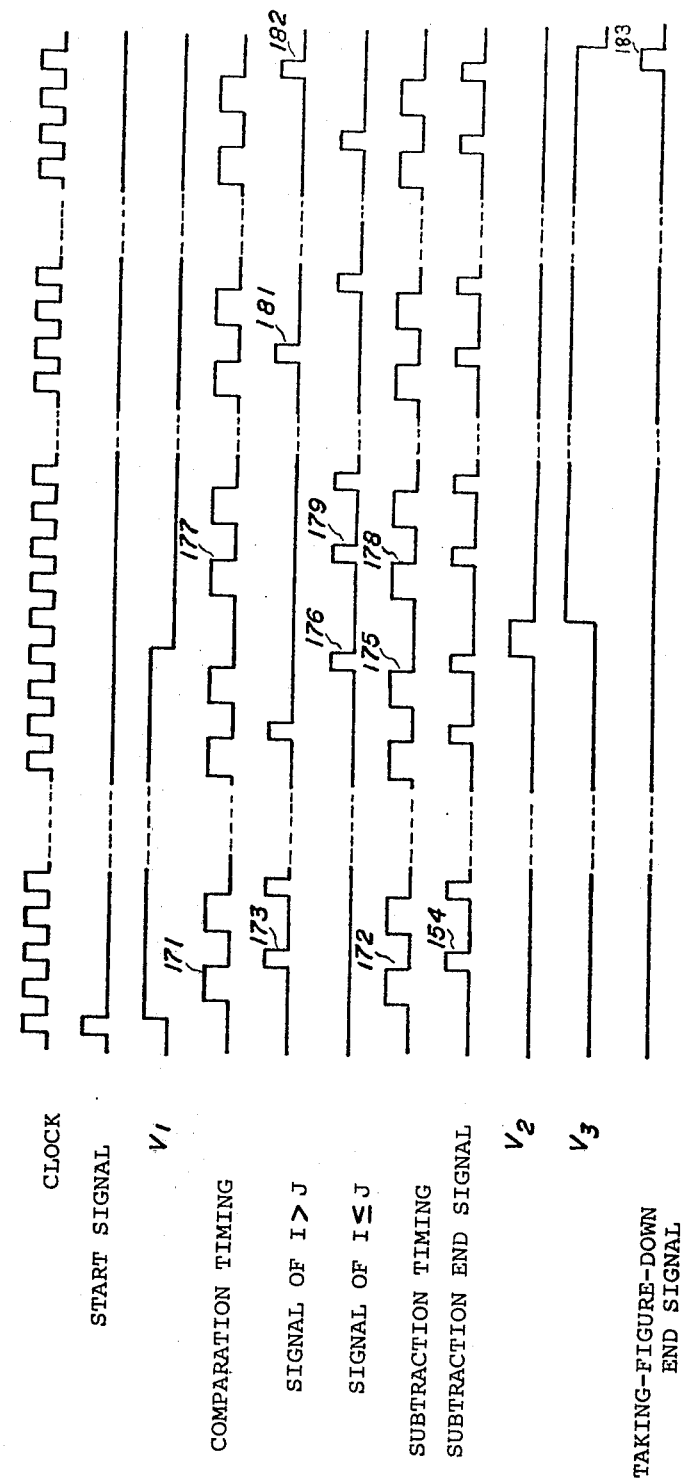
FIG. 16 is a time chart of various signals occurring in the lineality compensation circuit illustrated in FIG. 15.

FIG. 15 depicts a circuit configuration of the lineality compensation circuit and FIG. 16 is a time chart of various signals occurring in the lineality compensation circuit shown in FIG. 15.

A memory 201 stores in the order of from K=0 to K=N the data of the polygonal line approximation function compensated by the variation compensation circuit shown in FIG. 13, the pressure value Pn, the found value Cn related to the pressure value Pn, and the found value $$An = \frac{Cn - Cn - 1}{Pn - Pn - 1}$$

per unit pressure. A register 259 contains the found value CM measured by the pressure sensor. The application of the start signal S permits an address counter 202 to set up "1". A register 264 receives found data C1 at the sectional points through gates 250, 261, and 263 according to the address directed by the address counter 202. A register 266 has the data CM from the register 259 through gates 260 and 265.

These data are transferred into a subtractor 273 and a comparator 274. The subtractor 273 functions to calculate the value of "C1−CM" and the comparator 274 serves to compare the magnitude therebetween in timing pulses 171 and 172. When CM>C1, a signal representative of I>J is developed at a timing pulse 173 to advance the address counter 202 by one e.g. to "2" through a gate 253. The results of the calculation carried out in the subtractor 273 are not utilized because a gate 262 is inconductive while CM>C1.

When the address counter becomes "2", data C2 is developed from the memory 201 to the register 264 to repeat the same procedures as the data C1. These procedures are maintained before CM≦Ck is established where CM is the data contained in a register 259 and CK is the data generated from the memory 201. When CM≦Ck, a signal indicative of I≦J is developed at at timing pulse 176. This signal makes a gate 262 conductive. At a timing pulse 175, the results calculated in the subtractor 273 are transmitted to a register 264. This means that the calculation of Ck−CM is completed.

The signal representative of I≦J makes gates 276 and 255 change from (V1, V2, V3) to (010). The condition of V2=1 is kept for one clock time period and, meanwhile, the data AK in the memory 201 are transferred into a register 266 through a gate 265. The data Pk are further trasmitted into a register 271 through a gate 252. The signal of V2=1 makes a register 272 set up a unit pressure. The condition of V2=1 is kept for one clock time period and, thereafter, it occurrs that the shift register 254 is changed to (001).

Under these circumstances, at the timing pulses 177 and 178, the data contained in the register 264 and 266 are transferred into the subtractor 273 and the comparator 274 which carry out the calculation of (Ck−CM)−AK and the comparison between (Ck−CM) and Ak, respectively. The contents of the register 271 and 272 are transmitted into a subtractor 275 to calculate Pk−(unit pressure).

When (Ck−CM)>AK, a signal representative of I≦J is developed at a timing pulse 179 to make gates 262 and 268 conductive. The results of the subtractor 273, e.g. the value of (Ck−CM)−AK are transferred into the register 264. The results of the subtractor 275, e.g. Pk−(unit pressure) are introduced into a register 271 through a gate 269. These procedures are repeated until (Ck−CM)−β1 Ak<Ak (β1 is the number of loops).

When the completion of the above procedures, a signal representative of I>J is generated from the comparator 274 at a calculation end timing pulse 181. The contents of register 266 and 272 are allowed to take figures down through a gate 267. The contents of the register 266 are the value of Ak×10$^{-1}$ at decimal and Ak×16$^{-1}$ at hexadecimal. The contents of the register 272 are common at this point.

The calculation procedures are carried out as previously mentioned. When a signal indicative of I>J is generated from a comparator 274, the contents of the down registers 266 and 272 are took so that each of them contains Ak×B$^{-2}$ and (unit pressure)×B$^{-2}$ where B is ten as the decimal and sixteen as the hexadecimal. The comparison and subtraction are still repeated.

After taking figures down at a predetermined number and the comparison and subtraction are completed, a signal 183 indicative of taking-figures-down completion is developed on a line 279 from a register 272 upon a signal 182 representative of I>J generated from the comparator 274. The signal 183 allows a shift register 254 to transfer to the condition of (000) through gate 257. The calculation for lineality compensation is completed. The results are held in a register 271. The calculation processed in the lineality compensation circuit 9 is represented according to the following equation:

$$(Ck - CM) - \sum_{j=0}^{J} \beta J A k B^{-J} > 0$$

where j is the number of taking figures down.

Using the value of $\beta j$ (j=0 to J), the pressure value PM is determined according to the following equation.

$$PM = Pk - \sum_{i=0}^{J} \beta i \text{ (unit pressure)} \times B^{-k}$$

The variation compensation circuit 8 and the lineality compensation circuit 9 can be incorporated into a semiconductor chip of a large scale integration within the knowledge of one skilled in the art.

While only certain embodiments of the present invention have been described, it will be apparent to those skilled in the art that various changes and modifications may be made therein without departing from the spirit and scope of the invention as claimed.

What is claimed is:

1. A sphygmomanometer comprising:
   pressure detection means for measuring the applied sphygmomanometric pressure and providing an output indicative of said pressure;
   means for producing signals indicative of pulsatile variations in arterial pressure in response to the variations in pressure;
   a non-linear correlation function circuit for providing a non-linear correction function and generating a correction signal for each pressure sensed by said pressure detection means;
   compensation circuit responsive to said correction signal for converting said output of said pressure detection means into a actual pressure value output; and
   means responsive to said means for producing signals indicative of pulsatile variations for selecting the corrected actual pressure value outputs from said compensation circuit to provide an indication of blood pressure.

2. The sphygmomanometer of claim 1 wherein said means for producing comprises:
   a korotkoff sound detector for producing signals representative of korotkoff sounds.

3. The sphygmomanometer of claim 2 wherein said korotkoff sound detector comprises:
   a microphone for sensing said korotkoff sounds and producing korotkoff sound signals in response thereto;
   pressure decrease determination means for determining a decrease in said measured pressure value by sensing a decrease in said signal generated by said blood pressure detection means and producing an output signal in response to the decrease; and
   processor means for producing signals indicative of pulsatile variations in response to said korotkoff sound signals and said signal produced by said pressure decrease determination means.

4. The sphygmomanometer of claim 3 wherein said pressure detection means generates a variable frequency signal indicative of said measured pressure value.

5. The sphygmomanometer of claim 4 wherein said pressure detection means includes a blood pressure cuff.

6. The sphygmomanometer of claim 1 wherein said non-linear correlation function circuit has a family of nonlinear correlation functions stored therein; and
   wherein a compensation code is presented to said non-linear correlation function to determine which of said family of non-linear correlation functions is to be used for generating said correction signals.

7. The sphygmomanometer of claim 6, wherein said compensacode is produced by the combination of:
   a reference pressure detector for sensing a reference pressure and generating an actual reference pressure value;
   means for determining the pressure output measured by said pressure detection means when supplied by said reference pressure value;
   means for generating a difference signal responsive to the difference between the actual reference pressure value sensed by said reference pressure detector and the pressure output measured by said means for determining; and
   means for generating a compensation code by selecting said non-linear correlation function nearest to said difference determined by said means for generating.

8. The sphygmomanometer of claim 7 wherein said actual reference pressure value approaches the maximum value expected to be measured by said sphygmomanometer.

* * * * *